United States Patent
Gill et al.

(10) Patent No.: US 9,402,749 B2
(45) Date of Patent: Aug. 2, 2016

(54) METHOD OF CONTROLLING A PROSTHESIS

(75) Inventors: Hugh Gill, Gleniffer Gate (GB);
Douglas Derek Smith, Paisley (GB);
Stuart Edgar Mead, Great Missenden (GB); Brian Nolan, Kilmarnock (GB)

(73) Assignee: TOUCH BIONICS LIMITED, Livingston, West Lothian (GB)

( * ) Notice: Subject to any disclaimer, the term of this patent is extended or adjusted under 35 U.S.C. 154(b) by 547 days.

(21) Appl. No.: 13/378,650

(22) PCT Filed: Jun. 23, 2010

(86) PCT No.: PCT/GB2010/001232
§ 371 (c)(1),
(2), (4) Date: May 10, 2012

(87) PCT Pub. No.: WO2010/149967
PCT Pub. Date: Dec. 29, 2010

(65) Prior Publication Data
US 2012/0221122 A1 Aug. 30, 2012

(30) Foreign Application Priority Data

Jun. 24, 2009 (GB) .................................. 0910920.8

(51) Int. Cl.
*A61F 2/58* (2006.01)
*A61F 2/68* (2006.01)
(Continued)

(52) U.S. Cl.
CPC . *A61F 2/68* (2013.01); *A61F 2/586* (2013.01);
*A61F 5/01* (2013.01); *A61F 2002/701*
(2013.01); *A61F 2002/7635* (2013.01); *A61F 2002/7645* (2013.01)

(58) Field of Classification Search
CPC .. B25J 9/0006; A61F 2/54; A61F 2002/6827;
A61F 2/58; A61F 2/586
USPC ........................................................ 623/57, 64
See application file for complete search history.

(56) References Cited

U.S. PATENT DOCUMENTS 2,669,727 A 2/1954 Opuszenski
3,866,246 A 2/1975 Seamone et al.
(Continued)

FOREIGN PATENT DOCUMENTS

CN 1803413 7/2006
EP 0145504 6/1985
(Continued)

OTHER PUBLICATIONS

Connolly, "Prosthetic hands from Touch Bionics," Industrial Robot: An International Journal, 35(4):290-293, 2008.
(Continued)

*Primary Examiner* — Bruce E Snow
(74) *Attorney, Agent, or Firm* — K&L Gates LLP

(57) ABSTRACT

The present invention relates to a method of controlling a movable component of a prosthesis or orthosis. The method (100) comprises moving the component by means of a motor (102) and determining when movement of the component is arrested when the component bears against a surface (104, 106). Thereafter a plurality of driving electrical pulses are applied to the motor (110) in dependence on the determination and when movement of the component is arrested to thereby drive the motor so as to cause the component to bear against the surface with greater force.

23 Claims, 5 Drawing Sheets

(51) Int. Cl.
*A61F 5/01* (2006.01)
*A61F 2/70* (2006.01)
*A61F 2/76* (2006.01)

(56) References Cited

U.S. PATENT DOCUMENTS

| | | | |
|---|---|---|---|
| 4,558,704 | A | 12/1985 | Petrofsky |
| 4,623,354 | A | 11/1986 | Childress et al. |
| 4,808,187 | A | 2/1989 | Patterson et al. |
| 4,955,918 | A | 9/1990 | Lee |
| 4,990,162 | A | 2/1991 | LeBlanc et al. |
| 5,413,611 | A | 5/1995 | Haslam, II et al. |
| 5,888,246 | A | 3/1999 | Gow |
| 6,344,062 | B1 | 2/2002 | Abboudi et al. |
| 7,370,896 | B2 | 5/2008 | Anderson et al. |
| 7,922,773 | B1 | 4/2011 | Kuiken |
| 8,662,552 | B2 | 3/2014 | Torres-Jara |
| 2003/0036805 | A1 | 2/2003 | Senior |
| 2004/0078091 | A1 | 4/2004 | Elkins |
| 2005/0192677 | A1 | 9/2005 | Ragnarsdottir et al. |
| 2006/0158146 | A1 | 7/2006 | Tadano |
| 2006/0167564 | A1 | 7/2006 | Flaherty et al. |
| 2006/0212129 | A1 | 9/2006 | Lake et al. |
| 2008/0146981 | A1 | 6/2008 | Greenwald et al. |
| 2008/0262634 | A1 | 10/2008 | Puchhammer |
| 2010/0016990 | A1 | 1/2010 | Kurtz |
| 2010/0116078 | A1 | 5/2010 | Kim |
| 2010/0274365 | A1 | 10/2010 | Evans et al. |

FOREIGN PATENT DOCUMENTS

| | | |
|---|---|---|
| EP | 1043003 | 10/2000 |
| GB | 1585256 | 2/1981 |
| GB | 2444679 | 6/2008 |
| GB | 0910920.8 | 3/2010 |
| JP | 53-11456 | 2/1978 |
| WO | WO 95/24875 A1 | 9/1995 |
| WO | 00/69375 | 11/2000 |
| WO | 03/017878 | 3/2003 |
| WO | 03/017880 | 3/2003 |
| WO | 2006/069264 | 6/2006 |
| WO | WO 2007/063266 A1 | 6/2007 |
| WO | 2007/076764 | 7/2007 |
| WO | 2007/076765 | 7/2007 |
| WO | 2007/127973 | 11/2007 |
| WO | 2008/044207 | 4/2008 |
| WO | 2008/098059 | 8/2008 |
| WO | WO 2008/098072 A2 | 8/2008 |
| WO | WO 2008/098072 A3 | 8/2008 |
| WO | 2010/018358 | 2/2010 |
| WO | PCT/GB2010/001232 | 10/2010 |
| WO | 2011/001136 | 1/2011 |
| WO | 2011/022569 | 2/2011 |
| WO | 2011/036473 | 3/2011 |
| WO | 2011/107778 | 9/2011 |
| WO | PCT/GB2010/001232 | 1/2012 |

OTHER PUBLICATIONS

Stix, "Phantom Touch: Imbuing a Prosthesis with Manual Dexterity," Scientific American, Oct. 1998, pp. 41 and 44.
Search Report for GB Application No. GB0916895.6 dated Mar. 17, 2010, 5 pages.
PCT International Search Report for PCT International Application No. PCT/GB2013/051961, mail date Dec. 11, 2013, 5 pages.
PCT International Search Report for PCT International Application No. PCT/GB2012/052021, mail date Nov. 26, 2012, 5 pages.
PCT Written Opinion of the International Searching Authority for PCT International Application No. PCT/GB2012/052021, mail date May 3, 2013, 6 pages.
PCT International Search Report for PCT International Application No. PCT/GB2012/052111, mail date Nov. 26, 2012, 5 pages.
PCT International Preliminary Report on Patentability for PCT International Application No. PCT/GB2010/051529, mail date Apr. 5, 2012, 7 pages.
PCT International Preliminary Report on Patentability for PCT International Application No. PCT/GB2011/050368, mail date Sep. 13, 2012, 7 pages.
PCT International Search Report and Written Opinion of International Searching Authority for PCT International Application No. PCT/GB2011/050368, mail date Jun. 21, 2011, 11 pages.
PCT International Search Report and Written Opinion of International Searching Authority for PCT International Application No. PCT/GB2010/051529, mail date Jan. 4, 2011, 11 pages.

METHOD OF CONTROLLING A PROSTHESIS

CROSS REFERENCE TO RELATED APPLICATIONS

This is a national phase under 35 U.S.C. §371 of International Application No. PCT/GB2010/001232, filed on Jun. 23, 2010, which claims priority to and the benefit of Great Britain Patent Application No. 0910920.8, filed on Jun. 24, 2009, the contents of each of which are incorporated by reference herein in their entirety.

FIELD OF THE INVENTION

The present invention relates to a method of controlling a movable component of a prosthesis or an orthosis and a prosthesis or orthosis comprising a movable component.

BACKGROUND TO THE INVENTION

Prosthetic hands with motor powered digits are known. For example, WO 2007/063266 describes a prosthesis with a mechanically operable digit that is moved by an electric motor. In the prosthesis of WO 2007/063266 the electric motor is located within the digit. The present inventor has appreciated shortcomings with known prostheses having motor driven digits, such as the prosthesis of WO 2007/063266.

STATEMENT OF INVENTION

The present invention has been devised in the light of the inventor's appreciation. According to a first aspect of the present invention, there is provided a method of controlling a movable component of a prosthesis or orthosis, the method comprising:
  moving the component by means of a motor;
  determining when movement of the component is arrested when the component bears against a surface; and
  providing at least one driving electrical pulse to the motor in dependence on the determination and when movement of the component is arrested to thereby drive the motor so as to cause the component to bear against the surface with greater force.

In use, the step of providing at least one driving electrical pulse to the motor causes the component (e.g. a digit of the prosthesis) to bear against the surface with greater force. The surface may, for example, be a surface of an object to be gripped between the digit and another digit, such as a thumb. Thus, for example, the step of providing at least one driving electrical pulse to the motor may cause a gripping force between the digit and the thumb to increase. The inventor has found that selection of an appropriate type or form of motor may increase the force by a moderate amount. In contrast, the method according to the present invention can increase the force by a considerable amount. For example, the inventor has found that in a known arrangement a force of about 1 kg can be achieved and that with application of the method of the present invention a force of up to 3.5 kg can be achieved.

The method of the present invention may find application in particular with arrangements in which the size and thus the motive power of the motor are constrained. More specifically, the motor may be contained in the component being moved. The component may be a digit of a hand prosthesis.

The at least one driving electrical pulse may be provided to the motor when movement of the component has substantially stopped. Thus, the step of determining when movement of the component is arrested may comprise determining when movement of the component is substantially stopped.

Alternatively or in addition, determining when movement of the component is arrested may comprise measuring an electrical signal passing through the motor. For example, the measured signal may comprise an electrical current drawn by the motor.

More specifically, determining when movement of the component is arrested may comprise comparing the measured electrical signal with a threshold value. The at least one driving electrical pulse may be provided to the motor in dependence on the comparison. For example, if the measured electrical signal is current drawn by the motor the at least one driving electrical pulse may be provided to the motor when the drawn current exceeds a threshold value of current. The exceeding of a threshold value of current may indicate that movement of the component is arrested. More specifically, the threshold value may be between substantially 500 mA and 1 A. More specifically, the threshold value may be substantially 700 mA.

Alternatively or in addition, the step of determining when movement of the component is arrested may comprise determining when movement is arrested after a period during which the component is moved by the motor.

Alternatively or in addition, the motor may comprise a direct current (d.c.) motor. More specifically, motor may comprise a permanent magnet direct current (d.c.) motor.

Alternatively or in addition, the step of moving the component may comprise providing a plurality of spaced apart electrical motive pulses to the motor.

More specifically, each of the plurality of spaced apart electrical motive pulses and the at least one driving electrical pulse may have a different period. More specifically, each of the plurality of spaced apart electrical motive pulses may have a period less than substantially a tenth of the period of the at least one driving electrical pulse. More specifically, each of the plurality of spaced apart electrical motive pulses may have a period less than substantially a hundredth of the period of the at least one driving electrical pulse. More specifically, each of the plurality of spaced apart electrical motive pulses may have a period less than substantially 0.1% of the period of the at least one driving electrical pulse.

Alternatively or in addition, each of the plurality of spaced apart electrical motive pulses may have a period of less than 1 mS ($1\times10^{-3}$ seconds). More specifically, each of the plurality of spaced apart electrical motive pulses may have a period of less than 250 μS ($1\times10^{-6}$ seconds). More specifically, each of the plurality of spaced apart electrical motive pulses may have a period of less than 125 μS. More specifically, each of the plurality of spaced apart electrical motive pulses may have a period of substantially 58 μS. Alternatively, each of the plurality of spaced apart electrical motive pulses may have a period of substantially 24 μS.

Alternatively or in addition, at least one motive pulse may be provided to the motor when the at least one driving electrical pulse is provided to the motor.

Alternatively or in addition, the method may comprise the step of delaying the provision of the at least one driving electrical pulse to the motor for a predetermined delay period after completion of the step of determining when movement of the component is arrested. Whether or not the step of delaying the provision of the at least one driving electrical pulse may be selectable by a user of the prosthesis or orthosis.

More specifically, the predetermined delay period may be substantially between 10 mS and substantially 4 seconds.

More specifically, the predetermined delay period may be between substantially 100 mS and substantially 2 seconds. More specifically, the predetermined delay period may be between substantially 200 mS and substantially 1 second. More specifically, the predetermined delay period may be substantially 500 mS.

Alternatively or in addition, the step of providing at least one driving electrical pulse may comprise providing a plurality of driving electrical pulses.

More specifically, the plurality of driving electrical pulses may be provided to the motor for at least substantially 0.5 seconds. More specifically, a plurality of driving electrical pulses may be provided to the motor for at least substantially 1 second.

Alternatively or in addition, the driving electrical pulses may have a period of between substantially 1 second and substantially 2 mS. Hence, the motor may be operated at a frequency that is out of the motor's "sweet-spot" or the optimum range of frequencies for its normal operation, such as during the moving of the component before application of the driving electrical pulses. More specifically, the driving electrical pulses may have a period of between substantially 200 mS and substantially 4 mS. More specifically, the driving electrical pulses may have a period of between substantially 100 mS and substantially 10 mS. More specifically, the driving electrical pulses may have a period of between substantially 50 mS and substantially 20 mS. More specifically, the driving electrical pulses may have a period of substantially 27.78 mS.

Alternatively or in addition, at least substantially twelve driving electrical pulses may be provided to the motor. More specifically, at least substantially twenty four driving electrical pulses may be provided to the motor. Alternatively or in addition, substantially thirty six driving electrical pulses may be provided to the motor.

Alternatively or in addition, a space between driving electrical pulses may be greater than an on time of at least one of the driving electrical pulses. More specifically, the on time of at least one of the driving electrical pulses may be less than substantially 75% of the period of the driving electrical pulses. Alternatively or in addition, the on time of at least one of the driving electrical pulses may be between substantially 40% and substantially 60% of the period of the driving electrical pulses. More specifically, the on time of at least one of the driving electrical pulses may be substantially 50% of the period of the driving electrical pulses. The on time may be defined as the period of during which a driving electrical pulse is greater than zero.

Alternatively or in addition, a driving electrical pulse may comprise a constant portion and a decaying portion, the constant portion being at substantially a same voltage over time and the decaying portion changing from the level of the constant portion to substantially zero over time.

More specifically, the constant portion may be substantially 50% of the driving electrical pulse on time and the decaying portion may be substantially 50% of the driving electrical pulse on time.

Alternatively or in addition, the method may comprise arresting, by means of a counter movement arrangement, movement of the component in a direction opposite the direction in which the component is moved by the motor.

More specifically, the counter movement arrangement may comprise first and second gear components that are configured such that when they mesh with each other they present a greater resistance to movement in relation to each in one direction than in another.

More specifically, one of the first and second gear components may comprise a plurality of teeth with each tooth being asymmetric. Hence, each of the plurality of teeth may be set at an angle less than 90 degrees from a surface of the gear component from which the tooth extends.

Alternatively or in addition, the first gear component may comprise a gear wheel and the second gear component may comprise a worm. The worm may comprise a plurality of teeth that extend at an angle greater than 2 degrees from a line extending perpendicularly of the axis of rotation of the worm. More specifically, the plurality of teeth may extend at an angle of substantially 6.34 degrees to the perpendicularly extending line.

Alternatively or in addition, the component may be mechanically coupled to the motor by a mechanical coupling such that, in use, the component is moved by the motor by way of the mechanical coupling. More specifically, the mechanical coupling comprises at least one of a gearbox, first and second bevel gears, and a gear wheel and worm.

Alternatively or in addition, the at least one driving electrical pulse may have a positive amplitude of between substantially 3 volts and substantially 12 volts. More specifically, the driving electrical pulse may have a positive amplitude of between substantially 5 volts and substantially 9 volts. More specifically, the driving electrical pulse may have a positive amplitude of about 7 volts, such as substantially 7.2 volts.

Alternatively or in addition, the driving electrical pulses that move the component may have a positive amplitude of between substantially 3 volts and substantially 12 volts. More specifically, the driving electrical pulses that move the component may have a positive amplitude of between substantially 5 volts and substantially 9 volts. More specifically, the driving electrical pulses that move the component may have a positive amplitude of about 7 volts, such as substantially 7.2 volts.

Alternatively or in addition, the gear wheel may be attached to a support member of the prosthesis or orthosis such that the gear wheel does not rotate with respect to the support member and the worm may be in engagement with the gear wheel such that when the motor is operated the component moves around the gear wheel. Alternatively or in addition, the motor may be coupled to a gearbox.

According to a second aspect of the present invention, there is provided a prosthesis or an orthosis comprising:
 a movable component;
 a motor operable to move the component; and
 electrical apparatus operative: to determine when movement of the component is arrested when the component bears against a surface; and to provide at least one driving electrical pulse to the motor in dependence on the determination and when movement of the component is arrested to thereby drive the motor so as to cause the component to bear against the surface with greater force.

Embodiments of the second aspect of the present invention may comprise one or more features of the first aspect of the present invention.

BRIEF DESCRIPTION OF THE DRAWINGS

The present invention will now be described by way of example only with reference to the following drawings, of which.

SPECIFIC DESCRIPTION

Figure 1:
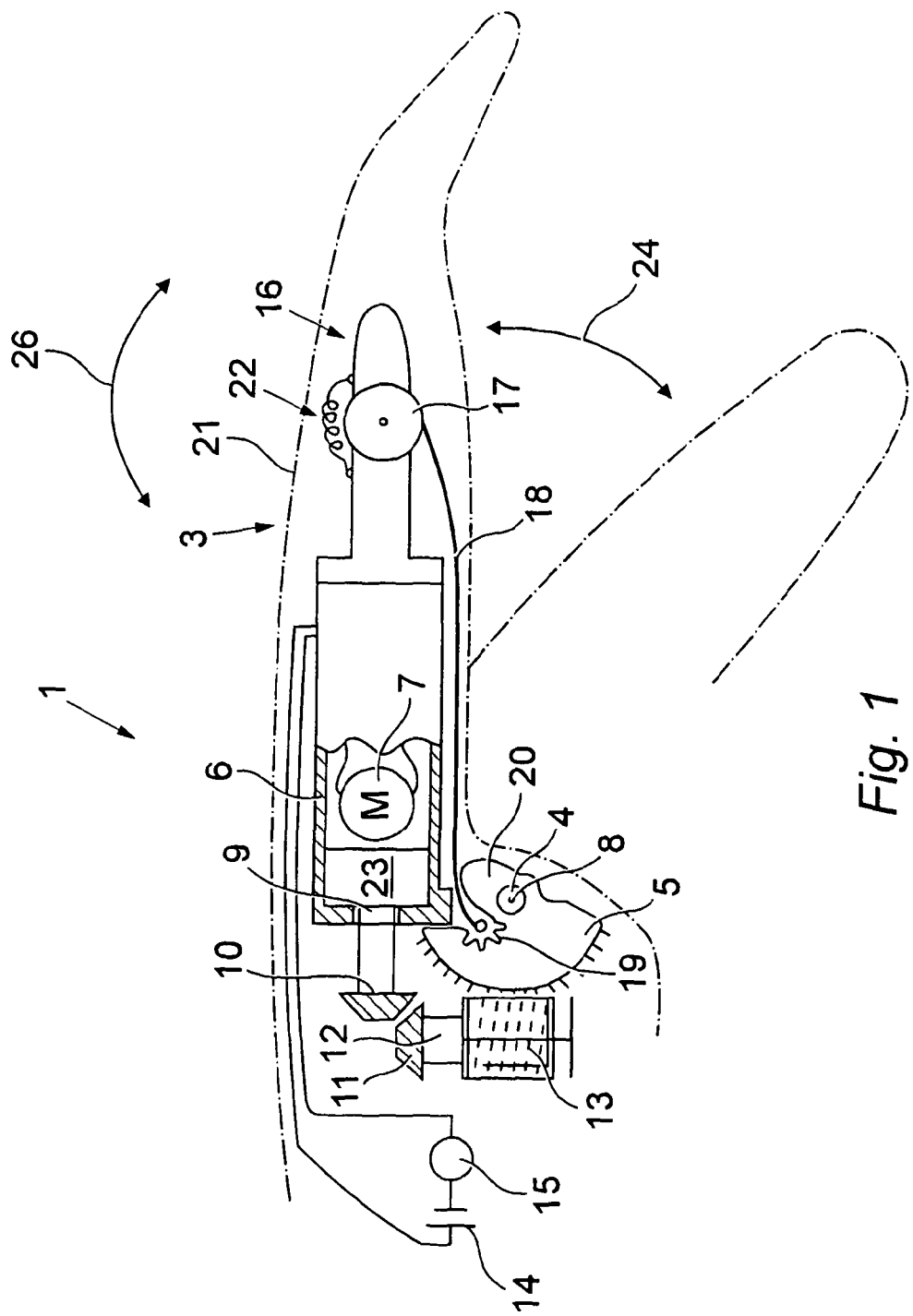
FIG. 1 is a partly cut-away view of a finger member of a prosthesis according to the present invention.

FIG. 1 shows a partly cut-away view of a hand prosthesis 1 having a finger 3 (which constitutes a component or digit). The prosthesis 1 is securely fixed in use to a patient's hand stump (not shown) in a generally known manner by means of a main body (not shown). The main body has a spindle 4 on which a gear wheel 5 is fixedly mounted. Gear wheel 5 is of roughly semi-circular profile. Finger 3 extends generally tangentially with respect to the gear wheel 5. Finger 3 has a generally tubular housing 6, in which is mounted a motor 7 having a gearbox system 23. The gearbox system 23 provides for different torque-output drive speed ratios to be selected from a range of different ratios. A GP 10 A Ø10 mm, 0.01 to 0.15 Nm planetary gearhead (order no. 218417) from Maxon Motor UK Limited, Maxon House, Hogwood Lane, Finchampstead, Berkshire RG40 4QW, UK is used in one form; this gearhead has a reduction ratio of 64:1. Lugs (not shown) depend from the underside of the tubular housing 6 and are rotatably mounted on the spindle to allow for rotation of the finger 3 in relation to the spindle 4 and gear wheel 5. The centre 8 of the spindle 4 defines an axis (which constitutes a gear wheel axis) about which the finger 3 rotates. The housing 6 containing the motor 7 corresponds to the proximal phalanx of a finger and the joint formed between the spindle 4 and the lugs depending from the housing 6 correspond to the metacarpophalangeal (MCP) or knuckle joint of a finger.

A drive shaft 9 extends from the motor 7 and gearbox system 23. A first bevel gear 10 is mounted on the distal end of the drive shaft 9. A second bevel gear 11 is mounted within the prosthesis 1 such that an axis of rotation of the second bevel gear 11 is at substantially 90 degrees to an axis of rotation of the first bevel gear 10. The gear ratio of the first and second bevel gears 10, 11 is substantially 1 to 1, although the gear ratio can be readily changed by known means. The second bevel gear 12 is mounted on the same shaft 12 as a worm 13. The worm 13 is located such that it engages with a toothed, curved peripheral edge of gear wheel 5. As can be seen from FIG. 1 the worm 13 extends laterally to the housing 6 at an angle of about 90 degrees. The worm and gear wheel have a 25:1 reduction ratio.

It should be noted that the worm 13 is located in the prosthesis such that it is outside the housing 6. Thus, the worm is located within the hand of the prosthesis and not the finger 3 even though the prosthesis is structured such that the worm 13 moves with the housing 6 upon operation of the finger 3, as described below.

The motor 7 is a permanent magnet DC motor having a substantially linear relation between torque and drive current. A Maxon RE 10 Ø10 mm, precious metal brushes, 1.5 Watt motor (order no. 118392, 118394 or 118396) from Maxon Motor UK Limited, Maxon House, Hogwood Lane, Finchampstead, Berkshire RG40 4QW, UK is used where a physically larger and more powerful motor is required. A Maxon RE 10 Ø10 mm, precious metal brushes, 0.75 Watt motor (order no. 118383, 118385 or 118386) from Maxon Motor UK Limited is used where a physically smaller and less powerful motor is required. In normal use the motor rotates at 21,000 rpm. The motor is powered by small rechargeable batteries 14, which may be mounted remotely of the prosthesis. The motor is controlled by means of switches 15, which are actuated by known means, e.g. residual digit movement or wrist movement. Alternatively or in addition, control may be by means of pressure sensitive resistors or signals derived from the electromyographic activity of residual muscle actions. In forms of the invention in which the prosthesis comprises a plurality of other digits, i.e. a thumb and one or more other fingers, control by known means provides for independence of movement of the digits or groups of digits. In the case of a finger or a thumb the motor 7 has low speed, high torque characteristics.

Finger 3 has a finger tip portion 16 corresponding to the middle and distal phalanges of a finger (and which constitutes a second digit member), which forms with the distal end of the housing 6 a proximal joint 17 corresponding to a proximal intermediate phalangeal (PIP) joint of a finger. Arrow 24 represents movement of the finger 3 about axis 8 (i.e. the MCP joint) and arrow 26 represents movement of finger tip portion 16 about PIP joint 17. An inextensible belt or chord 18 is attached at a first end to the gear wheel 5 in an aperture 19 provided in the gear wheel 5, passes over a protrusion 20 formed on the gear wheel and is attached at a second end to the finger tip portion 16. A helical spring 22 is connected at one end to the end of housing 6 and at a second opposing end to the finger tip portion 16. The prosthesis is clad in a known manner with an overlay 21 of silicone rubber or the like to provide an aesthetically acceptable appearance which is as similar as practicable to a normal hand.

The hand prosthesis 1 further comprises a circuit board containing electronic circuitry (which constitutes electrical apparatus), which is operative to control operation of the motor as described in detail below. The electronic circuitry comprises a TMS320F2808ZGMA, which is a 32-bit digital signal controller from Texas Instruments, and a flash memory IC. The design of circuitry based on and around the digital signal controller and the flash memory will be readily within the grasp of the ordinary design capabilities of the skilled person. The control processes described below are embodied in firmware, which is stored in and executed on the digital signal controller and the flash memory IC. The electronic circuitry also comprises an H-bridge, which is used to provide for bi-directional drive of the motor, and a current measurement circuit, such as a MAX4073 from Maxim Integrated Products, which is configured to measure current drawn through the H-bridge. The H-bridge will be well known to the skilled person and the design of circuitry based on the H-bridge and the current measurement circuit will be readily within the grasp of the ordinary design capabilities of the skilled person.

In use the wearer actuates the finger by one of the means described above, e.g. by way of electromyographic activity of residual muscle actions. Operation of the motor 7 in response to actuation causes rotation of the first bevel gear 10, which rotates the second bevel gear 11 together with the worm 13. As the worm 13 rotates it progresses around the peripheral surface of the fixed gear wheel 5 either clockwise or anti-clockwise depending on the direction of rotation of the motor 7. This moves the finger 3 about the axis 8 in the direction indicated by arrow 24. As finger 3 moves about axis 8 in a downward direction the distance between the point of attachment of the belt 18 in aperture 19 of the worm gear wheel 5 and the proximal joint 17 reduces. This is because aperture 19 is offset from the axis of the gear wheel as shown in FIG. 1. As the distance reduces the fixed length belt 18 pulls on the finger tip portion 16 against the bias of the helical spring 22 to rotate the finger tip portion 16 clockwise in relation to the rest of the finger 3. Upon reversal of the direction of rotation of the finger 3 about the axis, i.e. movement of finger 3 upwards, tension is released on the belt 18 and the spring 22 exerts a bias on the finger tip portion 16 to return the finger tip portion to the extended position shown in FIG. 1.

Figure 2:
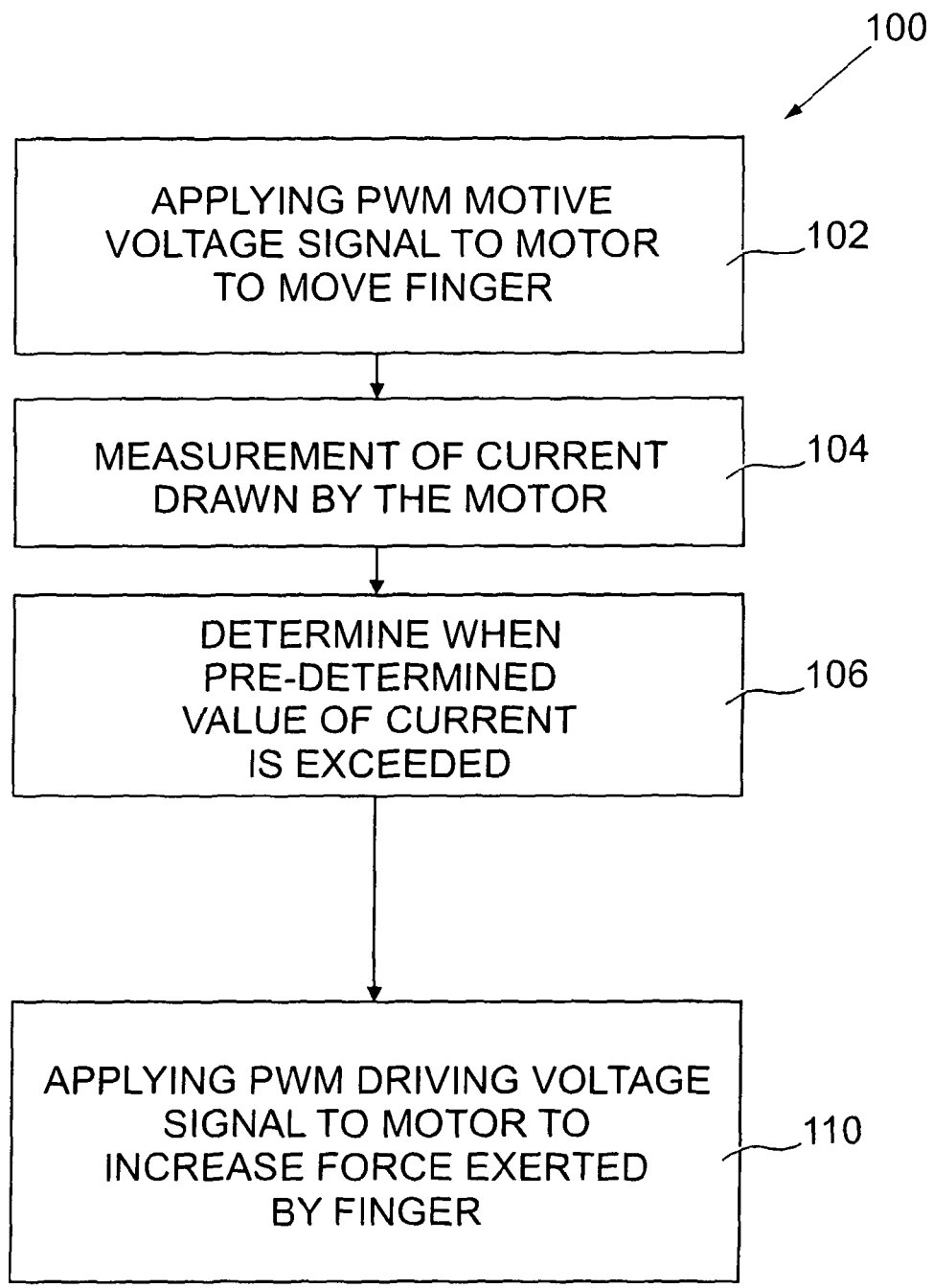
FIG. 2 is a flow chart representation of certain procedural steps performed by the prosthesis.
Figure 3:
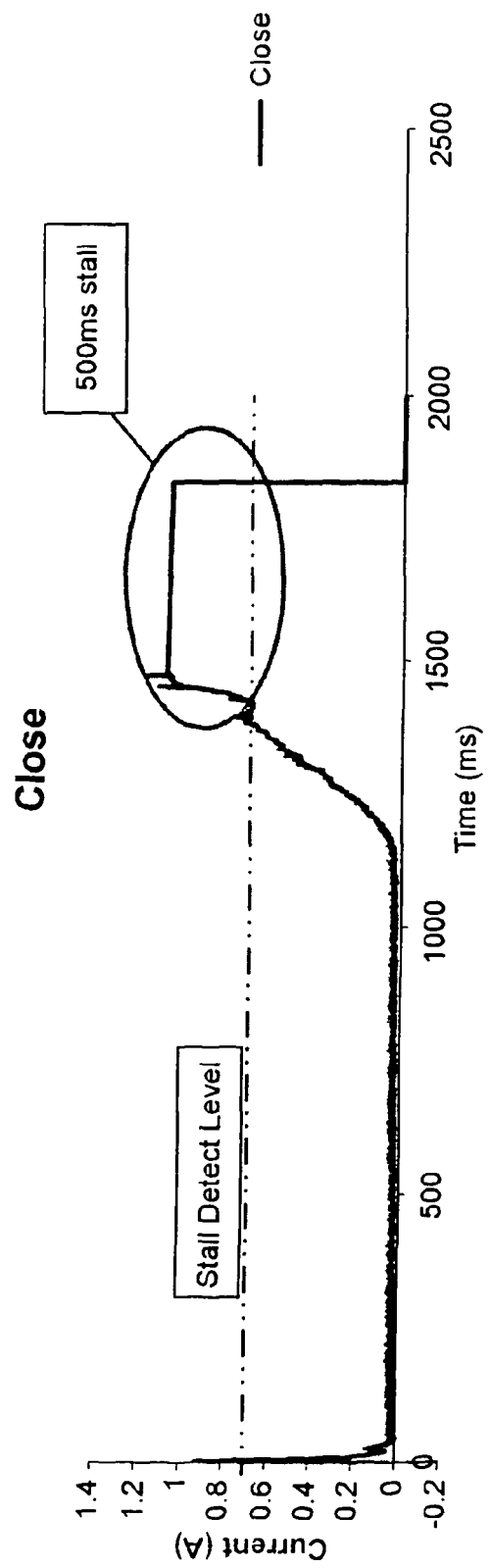
FIG. 3 shows the level of current drawn by the motor over time.

Further operation of the prosthesis will now be described with reference to FIG. 2, which is a flow chart representation 100 of procedural steps performed by the prosthesis. Movement of the finger 3 (which constitutes a component of a prosthesis or orthosis) by means of the motor 7 in a first direction may, depending on how the prosthesis is being used, cause the finger tip portion 16 to bear against a surface, such as a surface of an object to be held between the finger 7 and a prosthetic thumb. Movement of the finger is achieved by the application of a pulse width modulated (PWM) motive voltage signal to the motor 102 (which constitutes a plurality of spaced apart electrical motive pulses). The mark to space ratio of the PWM motive voltage signal is varied depending on the level of electrical power that is required to be delivered to the motor. The PWM motive voltage signal has a frequency of 41.6 kHz. As the finger tip portion 16 grips the object (which constitutes bearing against a surface), movement of the finger is arrested. As finger movement is arrested, there is a progressive increase in the current drawn by the motor 7 through the H-bridge. The progressive increase in the current drawn by the motor 7 is shown in FIG. 3, which shows the level of current drawn by the motor over time. The current drawn by the motor 7 is measured by the current measurement circuit 104 and compared with a predetermined value of current stored in the digital signal controller. As can be seen from FIG. 3 the predetermined level of current is substantially 700 mA. When the predetermined value of current is exceeded 106, the digital signal controller commences a 500 mS delay. After the 500 mS delay, a pulse width modulated (PWM) driving voltage signal (which constitutes a plurality of driving electrical pulses) is applied 110 to the motor 7. In another form, no 500 mS delay is applied and the pulse width modulated (PWM) driving voltage signal is applied when the predetermined value of current is exceeded. Selection between applying the delay and not applying the delay is made by the user depending on his or her preference or requirements. Selection by the user is by way of a Graphical User Interface (GUI) on a Personal Computer (PC), the prosthesis or orthosis having a communications port that provides for communication of configuration data with the PC. The design of necessary communications hardware and firmware and the design of a PC resident GUI will be readily within the grasp of the ordinary design capabilities of the skilled person.

Figure 4:
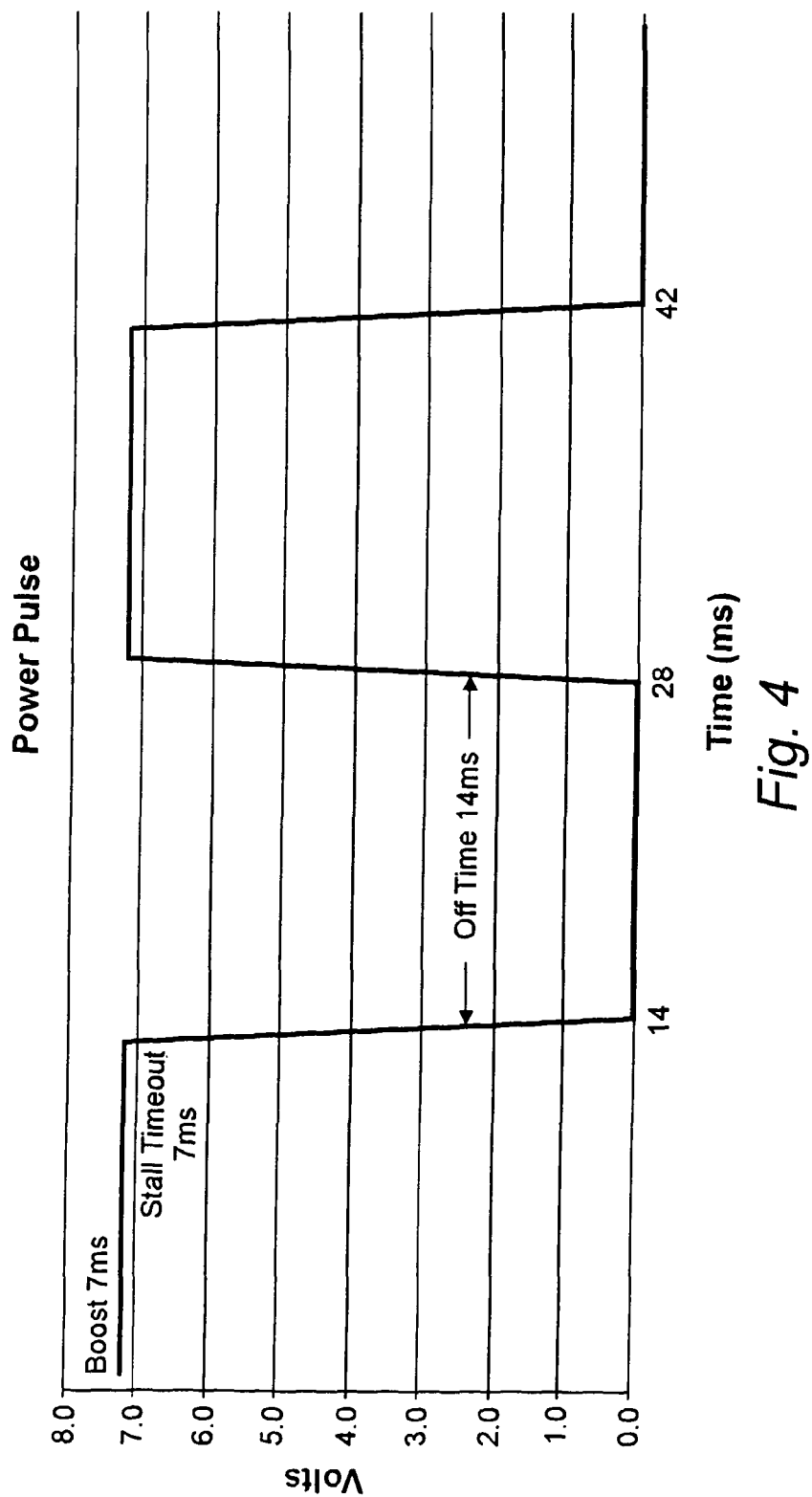
FIG. 4 shows an example of a PWM driving voltage pulse over time.
Figure 5:
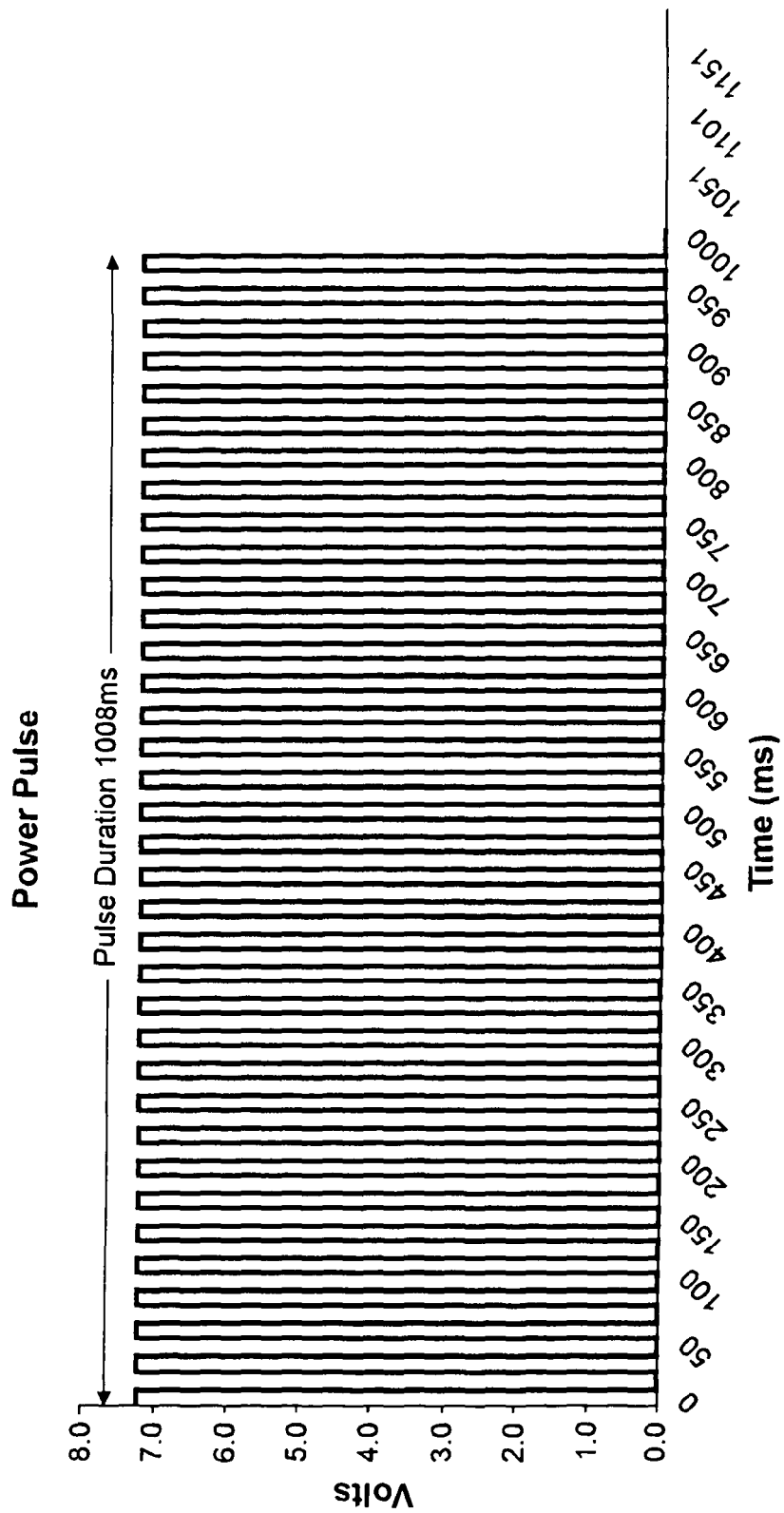
FIG. 5 shows a series of PWM driving voltage pulses over time.

The PWM driving voltage signal has a frequency of substantially 36 Hz and has a mark to space ratio of substantially one to substantially one. During the first half of the mark or on-time of the driving voltage signal (which constitutes the constant portion), the voltage level is substantially constant. During the second half of the mark or on-time of the driving voltage signal (which constitutes the decaying portion), the voltage level changes progressively from the level of the first half to substantially zero. FIG. 4 shows an example of a PWM driving voltage pulse over time according to a form in which there is no decaying portion such that the on-time consists of a constant portion. The inventor has found that application of the PWM driving voltage signal to the motor increases the force exerted by the finger beyond the level achievable by application of the PWM motive voltage signal alone. FIG. 5 shows 36 driving pulses being applied to the motor. The greater duration of pulse application, i.e. the larger number of pulses applied, progressively increases the force applied by the finger. For example, application of the PWM driving voltage signal for 3 seconds causes the finger to exert a force of substantially 3.5 kg whereas application of the PWM motive voltage signal alone achieves a force of 1 kg.

Counter movement of the finger before, during and after the application of the PWM driving voltage signal is resisted by the configuration of the gear wheel and the worm. More specifically, the teeth of the worm extend at an angle of substantially 6.34 degrees from a line extending perpendicularly of the axis of rotation of the worm. When the teeth of the gear wheel and the worm mesh with each other, the angle of the teeth of the worm provides for a greater resistance to movement of the finger in a direction opposing the direction in which the finger exerts its force than in the direction in which the finger exerts its force.

The procedural steps described above are embodied in firmware, which is resident in and executed on the digital signal controller. The creation of such firmware is within the ordinary design capabilities of the skilled person.

The invention claimed is:

1. A method of increasing the force applied by a movable component of a prosthesis or orthosis against a surface, the method comprising:
    moving the component by providing a plurality of spaced apart electrical motive pulses supplied to a motor driving a worm gear having a plurality of teeth that extend at an angle greater than 2° and less than 10° as measured from a line perpendicular to the axis of rotation of the worm and configured to drive the movable component;
    determining when movement of the component is arrested when the component bears against the surface; and
    providing a plurality of driving electrical pulses to the motor in response to the determination that the movement of the component is arrested,
    wherein the plurality of motive electrical pulses have a frequency more than 1000 times higher than the frequency of the driving pulses, to thereby drive the motor so as to cause the component to bear against the surface with greater force.

2. The method according to claim 1, in which the motor is contained in the component being moved.

3. The method according to claim 1, in which the component is a digit of a hand prosthesis.

4. The method according to claim 1, in which the first of the plurality of driving electrical pulses are provided to the motor when movement of the component has substantially stopped.

5. The method according to claim 1, in which determining when movement of the component is arrested comprises measuring an electrical signal passing through the motor.

6. The method according to claim 5, in which determining when movement of the component is arrested comprises comparing the measured electrical signal with a threshold value.

7. The method according to claim 1, in which the step of determining when movement of the component is arrested comprises determining when movement is arrested after a period during which the component is moved by the motor.

8. The method according to claim 1, in which the motor comprises a direct current motor.

9. The method according to claim 1, in which each of the plurality of spaced apart electrical motive pulses has a period of less than 1 mS.

10. The method according to claim 1, in which no motive pulse is provided to the motor when the at least one driving electrical pulse is provided to the motor.

11. The method according to claim 1, further comprising the step of delaying the provision of the at least one driving electrical pulse to the motor for a predetermined delay period after completion of the step of determining when movement of the component is arrested.

12. The method according to claim 11, in which the predetermined delay period is between substantially 10 mS and substantially 4 seconds.

13. The method according to claim 1, in which the plurality of driving electrical pulses are provided to the motor for at least substantially 0.5 seconds.

14. The method according to claim 1, in which the driving electrical pulses have a period of between substantially 1 second and substantially 2 mS.

15. The method according to claim 14, in which the driving electrical pulses have a period of between substantially 50 mS and substantially 20 mS.

16. The method according to claim 1, in which a space between driving electrical pulses is greater than an on time of at least one of the driving electrical pulses.

17. The method according to claim 1, in which the on time of at least one of the driving electrical pulses is substantially 50% of the period of the driving electrical pulses.

18. The method according to claim 1, in which a driving electrical pulse comprises a constant portion and a decaying portion, the constant portion being at substantially a same voltage over time and the decaying portion changing from the level of the constant portion to substantially zero over time.

19. The method according to claim 18, in which the constant portion is substantially 50% of the driving electrical pulse on time and the decaying portion is substantially 50% of the driving electrical pulse on time.

20. The method according to claim 1, in which the method comprises arresting, by means of a counter movement arrangement, movement of the component in a direction opposite the direction in which the component is moved by the motor.

21. The method according to claim 20, in which the counter movement arrangement comprises first and second gear components that are configured such that when they mesh with each other they present a greater resistance to movement in relation to each in one direction than in another.

22. The method according to claim 21, in which one of the first and second gear components comprises a plurality of teeth with each tooth being asymmetric.

23. The method according to claim 1, in which the component is mechanically coupled to the motor by a mechanical coupling such that, in use, the component is moved by the motor by way of the mechanical coupling, the mechanical coupling comprising at least one of: a gearbox; a first bevel gear and a second bevel gear that mesh with each other; and a gear wheel and a worm that mesh with each other.

* * * * *